United States Patent
Zhang et al.

(10) Patent No.: US 12,240,821 B2
(45) Date of Patent: Mar. 4, 2025

(54) INHIBITORS OF GUANOSINE MONOPHOSPHATE SYNTHETASE AS THERAPEUTIC AGENTS

(71) Applicant: University of Southern California, Los Angeles, CA (US)

(72) Inventors: Chao Zhang, Los Angeles, CA (US); Feng Ni, Los Angeles, CA (US); Arunika Ekanayake, Los Angeles, CA (US); Biancha Espinosa, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 878 days.

(21) Appl. No.: 17/274,736

(22) PCT Filed: Jul. 12, 2019

(86) PCT No.: PCT/US2019/041635
§ 371 (c)(1),
(2) Date: Mar. 9, 2021

(87) PCT Pub. No.: WO2020/055504
PCT Pub. Date: Mar. 19, 2020

(65) Prior Publication Data
US 2022/0048866 A1 Feb. 17, 2022

Related U.S. Application Data

(60) Provisional application No. 62/730,871, filed on Sep. 13, 2018.

(51) Int. Cl.
C07D 239/94 (2006.01)
A61K 31/167 (2006.01)
(Continued)

(52) U.S. Cl.
CPC .......... *C07D 239/94* (2013.01); *A61K 31/167* (2013.01); *A61K 31/517* (2013.01);
(Continued)

(58) Field of Classification Search
CPC ..... C07D 239/94; A61P 35/00; A61K 31/167; A61K 31/517; A61K 45/06; C07C 235/56; C07C 237/42
See application file for complete search history.

(56) References Cited

U.S. PATENT DOCUMENTS

| 5,439,895 | A | | 8/1995 | Lee et al. |
| 5,616,582 | A | * | 4/1997 | Barker ................. C07D 239/94 544/231 |

(Continued)

OTHER PUBLICATIONS

Pubchem CID 231483, Create Date: Mar. 26, 2005, Date Accessed: Oct. 29, 2019, Compound Listed, p. 2.
(Continued)

*Primary Examiner* — Clinton A Brooks
*Assistant Examiner* — Jerica Katlynn Wilson
(74) *Attorney, Agent, or Firm* — DLA Piper LLP (US)

(57) ABSTRACT

The invention provides a series of GMPS enzyme inhibitors. The invention includes potent GMPS inhibitors that specifically and covalently bind to GMPS, exhibit broad anti-cancer activity, block the infection efficiency of viruses, and have the potentials to suppress undesired immune responses. These novel inhibitors of GMPS, and their derivatives, have tremendous potentials to be used as therapeutic agents for the treatment of cancers, viral infection and immune disorders.

6 Claims, 3 Drawing Sheets

(51) Int. Cl.
*A61K 31/517* (2006.01)
*A61K 45/06* (2006.01)
*A61P 35/00* (2006.01)
*C07C 235/56* (2006.01)
*C07C 237/42* (2006.01)

(52) U.S. Cl.
CPC .............. *A61K 45/06* (2013.01); *A61P 35/00* (2018.01); *C07C 235/56* (2013.01); *C07C 237/42* (2013.01)

(56) References Cited

U.S. PATENT DOCUMENTS

| | | |
|---|---|---|
| 6,613,772 B1 | 9/2003 | Schindler et al. |
| 2009/0036420 A1* | 2/2009 | Galley ................. C07C 237/40 548/950 |

OTHER PUBLICATIONS

Pubchem CID 5328827, Create Date: Jan. 30, 2006, Date Accessed: Oct. 29, 2019, Compound Listed, p. 2.

* cited by examiner

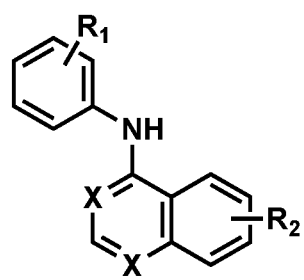
I
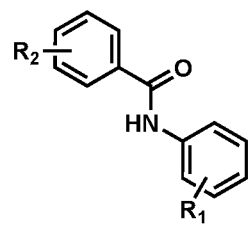
II
General Structures
FIGURE 2
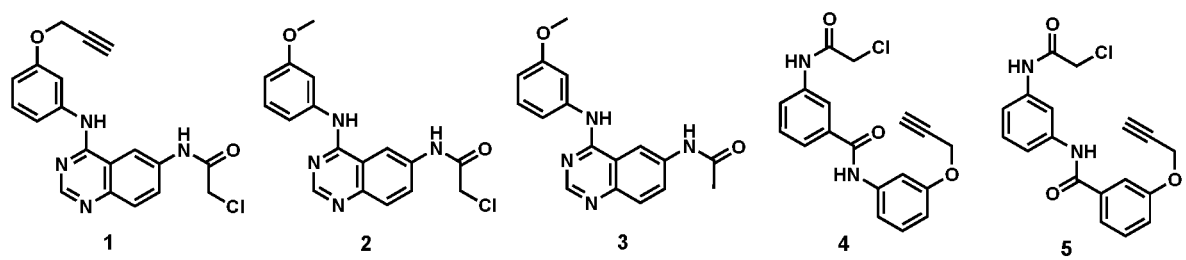
Compound structures
FIGURE 3

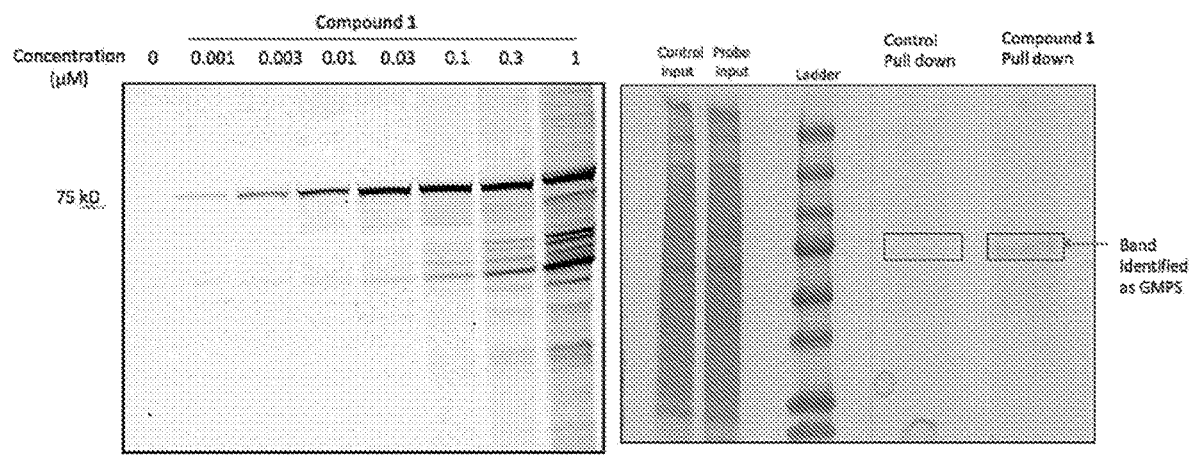
FIGURE 4A                               FIGURE B
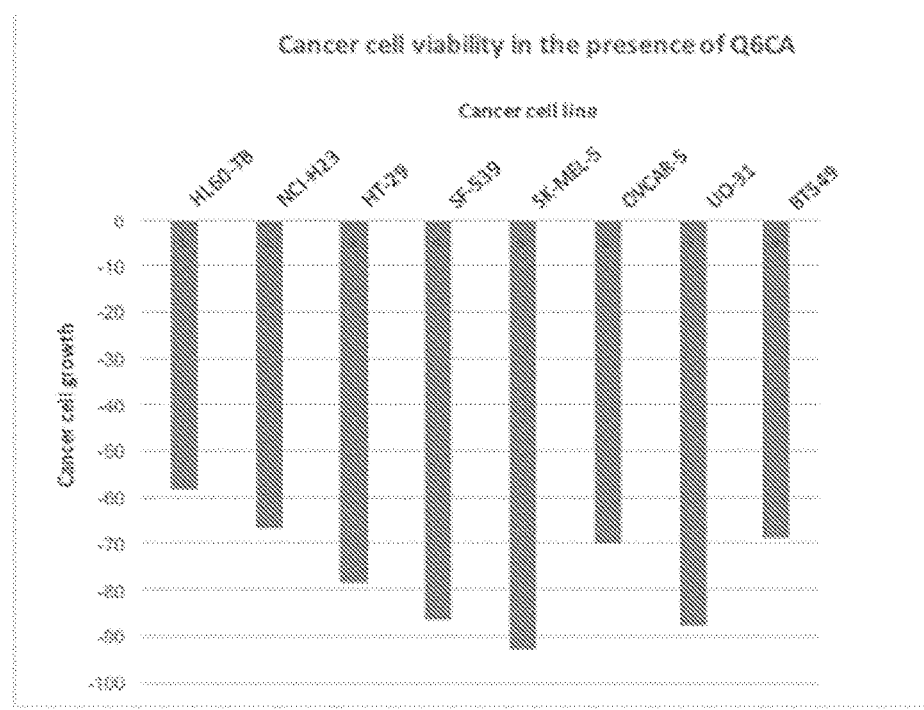
FIGURE 5

INHIBITORS OF GUANOSINE MONOPHOSPHATE SYNTHETASE AS THERAPEUTIC AGENTS

CROSS-REFERENCE TO RELATED APPLICATIONS

This application is a 35 USC § 371 National Stage application of International Application No. PCT/US2019/041635 filed Jul. 12, 2019, now pending; which claims the benefit under 35 USC § 119 (e) to U.S. Application Ser. No. 62/730,871 filed Sep. 13, 2018. The disclosure of each of the prior applications is considered part of and is incorporated by reference in the disclosure of this application.

GOVERNMENT SUPPORT

This invention was made with government support under grant CHE-1455306 awarded by the National Science Foundation. The government has certain rights in the invention.

BACKGROUND OF THE INVENTION

Field of the Invention

The present invention relates generally to guanosine monophosphate synthetase inhibitors, and more specifically to the use of novel inhibitors of guanosine monophosphate synthetase for the treatment of diseases or disorders and as immunosuppressive agents.

Background Information

The de novo biosynthesis pathway of the guanosine monophosphate (GMP) involves the conversion of inosine monophosphate (IMP) first to xanthosine monophosphate (XMP) and subsequently to GMP, with the latter step being catalyzed by an enzyme, guanosine monophosphate synthetase (GMPS). GMPS is a bi-domain enzyme that consists of a glutamine amidotransferase domain (GAT) and a synthetase domain. The GAT domain hydrolyzes glutamine to generate ammonia, which is transferred to the synthetase domain for reaction with a nucleotide intermediate to yield GMP, an essential precursor and building block for RNA and DNA in cells. Accordingly, GMPS plays important roles in cell division and proliferation as well as viral infection.

Human GMPS synthetase has been identified as a potential target for anticancer therapies. GMPS levels have been shown to be increased in metastatic melanoma cells comparing to primary melanoma. A number of studies document an important role that GMPS plays in tumor invasion of human metastatic melanomas. Importantly, it was demonstrated that GMPS inhibition led to diminution of tumor invasion and tumorigenesis.

GMPS has also been identified as an attractive target for immunosuppressive therapies, particularly in the clinical settings of organ transplantation and lupus. One of the main strategies used for immunosuppression involves suppression of the de novo purine synthesis pathway, specifically the de novo GMP synthesis inhibition to prevent GTP and dGTP generation. While the salvage pathway is able to generate some GMP upon blockade of the de novo synthesis in many cell types, the B and T lymphocytes lack important enzymes of the salvage pathway and largely depends on de novo purine biosynthesis for proliferation.

In addition to its roles in cancer and immunity described above, GMPS regulates viral infection. As an essential player in the de novo GMP biosynthesis, GMPS produces a large pool of purine nucleotides, which is required for the duplication of viral genome. It is thus thought that inhibition of GMPS would counter viral infection.

The existing inhibitors of GMPS are either glutamine analogues or nucleoside analogues, that mimic and compete with the substrates for binding to the active sites of GMPS. For example, acivicin is a glutamine analogue that inhibits GMPS through covalent binding to the GAT domain. Because there are multiple enzymes utilizing glutamine or nucleotide as substrates, these substrate-mimicking inhibitors tend to bind to multiple enzymes and exhibit low selectivity toward GMPS. This underlies the toxicity of numerous GMPS inhibitors when they were evaluated for therapeutic application in the past. The lack of potent and specific inhibitors of GMPS severely limits the exploitation of GMPS as a target in therapeutic application.

SUMMARY OF THE INVENTION

The present invention is based on the seminal discovery of novel inhibitors of guanosine monophosphate synthetase and the use of the inhibitors for the treatment of diseases and disorders, including cancer and viral infections. Additionally, the disclosed inhibitors can be used to suppress an immune response in a subject.

In one embodiment, the present invention provides a compound of Formula (I)

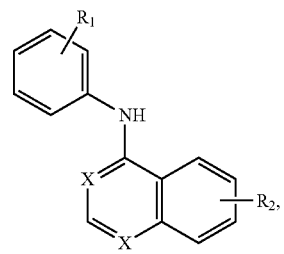

I or an optically pure stereoisomer or pharmaceutically acceptable salt thereof, wherein X is N or CH, R1 is an alkyl, acyl, alkoxy, halo, amino, amido, alkenyl, or alkynyl; and R2 is an alkyl, acyl; alkoxy, halo, amino, amido, alkenyl, or alkynyl.

In another embodiment, the invention provides a compound of Formula (II)

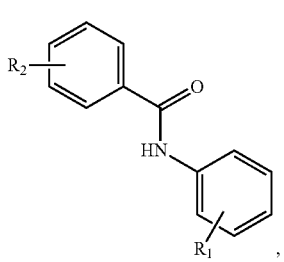

II or an optically pure stereoisomer or pharmaceutically acceptable salt thereof, wherein R1 is an alkyl, acyl, alkoxy, halo, amino, amido, alkenyl, or alkynyl; and R2 is an alkyl, acyl, alkoxy, halo, amino, amido, alkenyl, or alkynyl.

In certain aspects, the compound is

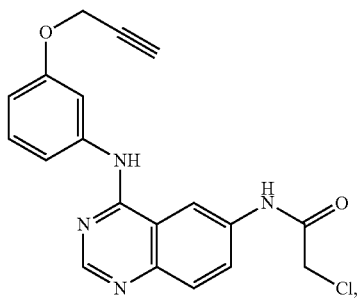

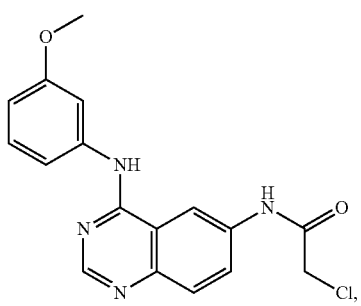

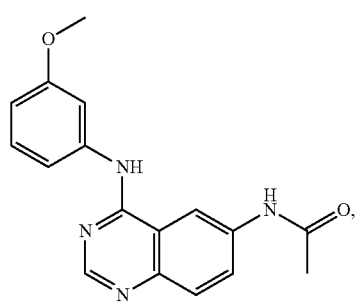

or a pharmaceutically acceptable salt thereof.
In other aspects, the compound is

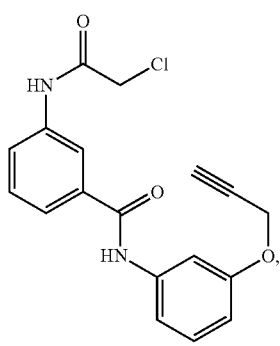

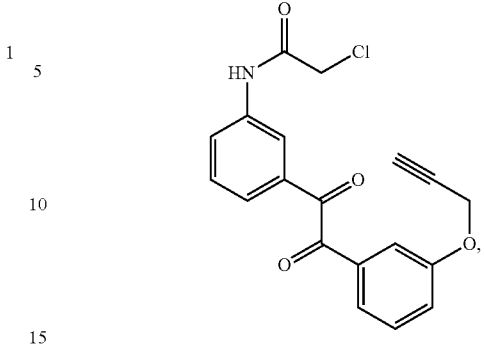

or a pharmaceutically acceptable salt thereof.

In certain aspects, the compound is 2-chloro-N-(4-((3-(prop-2-yn-1-yloxy)phenyl)amino)quinazolin-6-yl)acetamide; 2-chloro-N-(4-((3-methoxyphenyl)amino)quinazolin-6-yl)acetamide; N-(4-((3-methoxyphenyl)amino)quinazolin-6-yl)acetamide; 3-(2-chloroacetamido)-N-(3-(prop-2-yn-1-yloxy)phenyl)benzamide; or N-(3-(2-chloroacetamido)phenyl)-3-(prop-2-yn-1-yloxy)benzamide.

In an additional embodiment, the invention provides a method for a treating disease or disorder in a subject by administering a compound of Formula (I) or Formula (II) as provided above, thereby treating the disease disorder. In one aspect, the compound is at least one of compounds 1-5 as provided above.

In various aspects, the disease or disorder is cancer or viral infection. In certain aspects, the cancer is leukemia, non-small cell lung cancer, colon cancer, central nervous system (CNS) cancer, melanoma, ovarian cancer, renal cancer and/or breast cancer. In other aspects, the viral infection is gastroenteritis, fatal encephalitis, encephalitis, fever, joint pain, meningitis, myocarditis, paralysis, hemorrhagic fever, thrombocytopaenia, common cold, mononucleosis, renal or respiratory syndrome, hepatitis, pneumonia, diarrhea, neurological disorder, skin lesions, skin lymphoma, AIDS, skin warts, genital warts, cervical cancer, leukemia, flu, rash, Merkel cell carcinoma, mumps, poliomyelitis, rubella, Pogosta disease, varicella, and/or variola. In an additional aspect, the method further includes administering a chemotherapeutic agent or an anti-viral agent. In various aspect, the compound is administered prior to, simultaneously with or following the administration of the chemotherapeutic agent or anti-viral agent. In certain aspects, the compound inhibits guanosine monophosphate synthetase.

In an additional embodiment, the invention provides a method of suppressing an immune response in a subject comprising administering a compound of Formula (I) or Formula (II) as provided above to the subject, thereby suppressing an immune response.

In one aspect, the disease or disorder is cancer or viral infection. In one aspect, the compound is at least one of compounds 1-5 as provided above. In various aspect, the subject has an autoimmune disorder, an inflammatory disorder, ankylosing spondylitis or an organ and tissue transplant. In certain aspects, the compound inhibits guanosine monophosphate synthetase.

In yet another embodiment, the invention provides a pharmaceutical composition comprising a compound of Formula (I) or Formula (II) as provided above and a pharmaceutically acceptable carrier. In one aspect, the compound is at least one of compounds 1-5 as provided above.

BRIEF DESCRIPTION OF THE DRAWINGS

FIG. 2 shows the general chemical structures of the novel GMPS inhibitors.

FIG. 3 shows the compound structures of five novel GMPS inhibitors.

FIGS. 4A-4B illustrate the potent and selective covalent binding of compound 1 to GMPS in live cells. A. SDS PAGE in-gel fluorescence image of whole cell labeling with compound 1 at various concentrations. B. Identification of the 75 kDa band as GMPS through liquid chromatography/mass spectrometry analysis.

FIG. 5 is a bar graph illustrating the survival of eight distinct cancer cell lines in the presence of compound 1. HL-60(TB): Leukemia; NCI-H23: Non-Small Cell Lung Cancer; HT29: Colon Cancer; SF-539: Central Nervous System Cancer; SK-MEL-5: Melanoma; OVCAR-5: Ovarian Cancer; UO-31: Renal Cancer; BT-549: Breast Cancer.

DETAILED DESCRIPTION OF THE INVENTION

Figure 1:
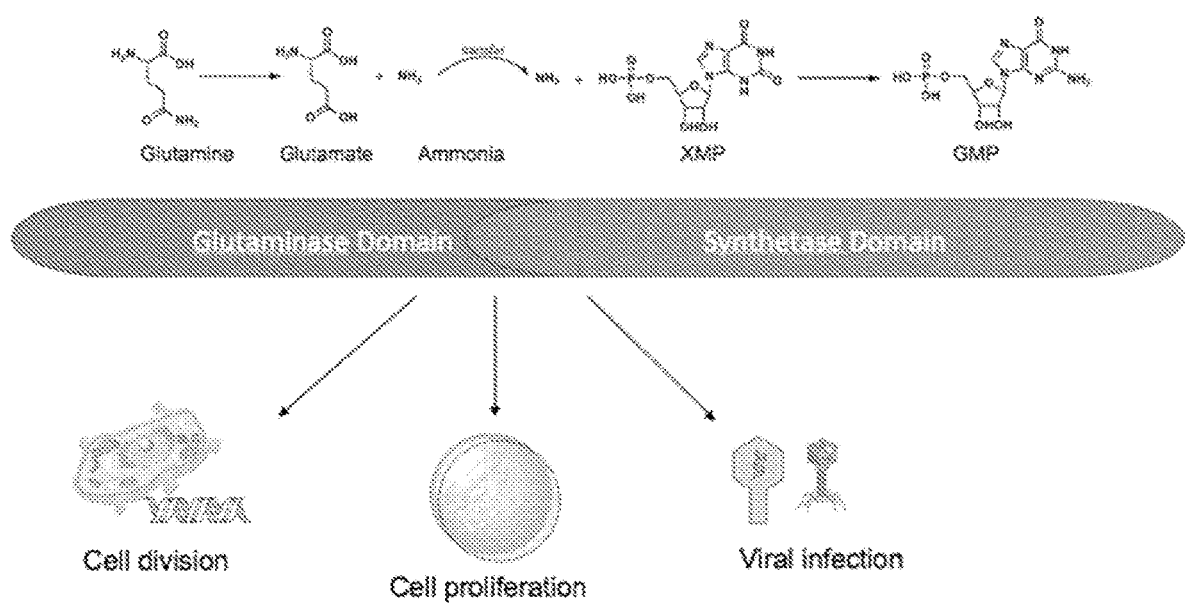
FIG. 1 is a schematic representation of the de novo biosynthesis pathway of GMP, illustrating the role of the bi-domain enzyme GMPS, and highlighting the roles of GMPS in cell division and proliferation as well as viral infection.

The present invention is based on the seminal discovery of novel inhibitors of guanosine monophosphate synthetase and the use of the inhibitors for the treatment of diseases and disorders, including cancer and viral infections. Additionally, the disclosed inhibitors can be used to suppress an immune response in a subject.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

The present invention is generally directed to small molecule inhibitors of guanosine monophosphate synthetase. Table 1 shows the structure of compounds of Formula (I) and Formula (II). Table 2 shows the structure of compounds 1-5.

TABLE 1

General structures

Formula (I)

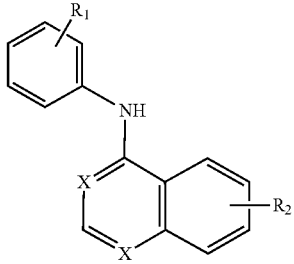

Formula (II)

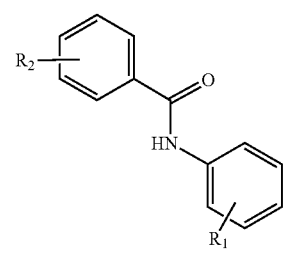

TABLE 2

Compounds structures

| Compound | Structure |
| --- | --- |
| 1 | 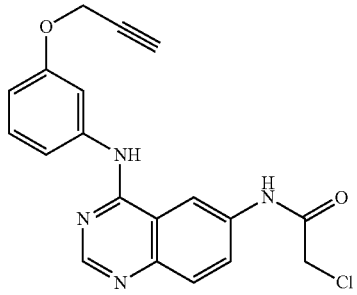 [SMILES: C#CCOc1cccc(Nc2ncnc3ccc(NC(=O)CCl)cc23)c1] |
| 2 | 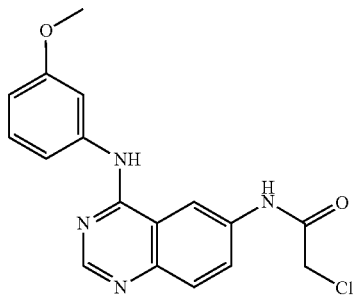 [SMILES: COc1cccc(Nc2ncnc3ccc(NC(=O)CCl)cc23)c1] |

TABLE 2-continued

Compounds structures

| Compound | Structure |
| --- | --- |
| 3 | (4-(3-methoxyphenylamino)quinazolin-6-yl)acetamide structure |
| 4 | N-(3-(2-(prop-2-yn-1-yloxy)phenylcarbamoyl)phenyl)-2-chloroacetamide structure |
| 5 | N-(3-(3-(prop-2-yn-1-yloxy)phenylamino)benzamide with chloroacetamide structure |

In one embodiment, the present invention provides a compound of Formula (I) or Formula (II), as provided in Table 1, or an optically pure stereoisomer or pharmaceutically acceptable salt thereof, wherein X is N or CH; R1 is an alkyl, acyl, alkoxy, halo, amino, amido, alkenyl, and alkynyl; and R2 is an alkyl, acyl, alkoxy, halo, amino, amido, alkenyl, and alkynyl.

As used herein, the term "Alkyl" refers to a straight or branched, saturated, aliphatic radical having the number of carbon atoms indicated. Alkyl can include any number of carbons, such as C1-2, C1-3, C1-4, C1-5, C1-6, C1-7, C1-8, C1-9, C1-10, C2-3, C2-4, C2-5, C2-6, C3-4, C3-5, C3-6, C4-5, C4-6 and C5-6. For example, C1-6 alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

As used herein, the term "Alkoxy" refers to an alkyl group having an oxygen atom that connects the alkyl group to the point of attachment: alkyl-O—. As for alkyl group, alkoxy groups can have any suitable number of carbon atoms, such as C1-6. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

As used herein, the term "Halogen" refers to fluorine, chlorine, bromine and iodine.

As used herein, the term "Haloalkyl" refers to alkyl, as defined above, where some or all of the hydrogen atoms are replaced with halogen atoms. As for alkyl group, haloalkyl groups can have any suitable number of carbon atoms, such as C1-6. For example, haloalkyl includes trifluoromethyl, flouromethyl, etc. In some instances, the term "perfluoro" can be used to define a compound or radical where all the hydrogens are replaced with fluorine. For example, perfluoromethane refers to 1,1,1-trifluoromethyl.

As used herein, the term "Haloalkoxy" refers to an alkoxy group where some or all of the hydrogen atoms are substituted with halogen atoms. As for an alkyl group, haloalkoxy groups can have any suitable number of carbon atoms, such as C1-6. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

As used herein, the term "Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)2-. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

As used herein, the term "Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as C3-6, C4-6, C5-6, C3-8, C4-8, C5-8, C6-8, C3-9, C3-10, C3-11, and C3-12. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic C3-8 cycloalkyl, exemplary groups include, but are not limited to cyclopropyl, cyclobutyl, cyclopentyl, cyclohexyl, cycloheptyl and cyclooctyl. When cycloalkyl is a saturated monocyclic C3-6 cycloalkyl, exemplary groups include, but are not limited to cyclopropyl, cyclobutyl, cyclopentyl, and cyclohexyl. Cycloalkyl groups can be substituted or unsubstituted.

As used herein, the term "Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Representative cycloalkylene groups include, but are not limited to, cyclopropylene, cyclobutylene, cyclopentylene, cyclohexylene, and cyclooctylene. Cycloalkylene groups can be substituted or unsubstituted.

As used herein, the term "Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)2-. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with C1-6 alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2-or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

As used herein, the term "Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention possess asymmetric carbon atoms (optical centers) or double bonds; the racemates, diastereomers, geometric isomers and individual isomers are all intended to be encompassed within the scope of the present invention.

As used herein, the term "Hydrate" refers to a compound that is complexed to at least one water molecule. The compounds of the present invention can be complexed with from 1 to 10 water molecules.

In certain aspects, the compound is at least one of compounds 1-5 as shown in Table 2 or an optically pure stereoisomer or pharmaceutically acceptable salt thereof. In an additional aspect, the compound is 2-chloro-N-(4-((3-(prop-2-yn-1-yloxy)phenyl)amino)quinazolin-6-yl)acetamide; 2-chloro-N-(4-((3-methoxyphenyl)amino)quinazolin-6-yl)acetamide; N-(4-((3-methoxyphenyl)amino) quinazolin-6-yl)acetamide; 3-(2-chloroacetamido)-N-(3-(prop-2-yn-1-yloxy)phenyl)benzamide; or N-(3-(2-chloroacetamido)phenyl)-3-(prop-2-yn-1-yloxy)benzamide.

In an additional embodiment, the invention provides a method for treating a disease or disorder in a subject including administering a compound of Formula (I) or Formula (II), as provided in Table 1 or an optically pure stereoisomer or pharmaceutically acceptable salt thereof to the subject, thereby treating the disease disorder. In one aspect, the compound is at least one of compounds 1-5 as shown in Table 2 or an optically pure stereoisomer or pharmaceutically acceptable salt thereof.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those needing preventive measures).

The term "subject" as used herein refers to any individual or patient to which the subject methods are performed. Generally the subject is human, although as will be appreciated by those in the art, the subject may be an animal.

The terms "therapeutically effective amount", "effective dose," "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. Such amount should be sufficient to inhibit GMPS enzymatic activity.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrastemal, oral, sublingual buccal, rectal, vaginal, nasal ocular administrations, as well infusion, inhalation, and nebulization.

In various aspects, the disease or disorder is cancer or viral infection.

The term "cancer" refers to a group of diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (OsteosarcomaVMalignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In certain aspects, the cancer is leukemia, non-small cell lung cancer, colon cancer, CNS cancer, melanoma, ovarian cancer, renal cancer and breast cancer. In other aspects, the viral infection is selected from the group consisting of gastroenteritis, fatal encephalitis, encephalitis, fever, joint pain, meningitis, myocarditis, paralysis, hemorrhagic fever, thrombocytopaenia, common cold, mononucleosis, renal or respiratory syndrome, hepatitis, pneumonia, diarrhea, neurological disorder, skin lesions, skin lymphoma, AIDS, skin warts, genital warts, cervical cancer, leukemia, flu, rash, Merkel cell carcinoma, mumps, poliomyelitis, rubella, Pogosta disease, varicella, and/or variola.

"Infectious disease" refers to a disease resulting from an infection. An infection is the invasion of an organism's body tissues by disease-causing agents, their multiplication, and the reaction of host tissues to the infectious agents and the toxins they produce. Infectious agents include viruses, viroids, prions, bacteria, nematodes such as parasitic roundworms and pinworms, arthropods such as ticks, mites, fleas, and lice, fungi such as ringworm, and other macroparasites such as tapeworms and other helminths. A short-term infection is an acute infection, accordingly and as used herein "chronic infection" refers to a long-term infection or to a persistent infection.

As used herein, "viral infection" refers to any infection or disease caused by a virus. Viruses responsible for viral infection include, but are not limited to, Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, Human enterovirus 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, Human papillomavirus 18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, and Zika virus.

In certain aspects, the compound inhibits guanosine monophosphate synthetase.

Guanosine monophosphate synthetase (GMPS) is a bi-domain enzyme that consists of a glutamine amidotransferase domain (GAT) and a synthetase domain. The GAT domain hydrolyzes glutamine to generate ammonia, which is transferred to the synthetase domain for reaction with a nucleotide intermediate to yield GMP. As used herein, the term "GMPS inhibitor" or "GMPSi" refers to any compound capable of inhibiting the enzymatic of GMPS, including the glutamine amidotransferase activity of the GAT domain and the synthetase activity of the synthetase domain. Such inhibitors efficiently inhibit GMPS, and are said to "inhibit", "decrease", or "reduce" the biological activity of GMPS.

The efficiency of a compound can be referred to by its IC50 value. The "IC50" is the half-maximal inhibitory concentration (IC50) of a compound. As used herein, the IC50 of a GMPSi refers to the concentration of inhibitor which is sufficient to induce the inhibition of the enzymatic activity of GMPS halfway between the baseline and maximum after a specified exposure time.

In an additional aspect, the method further includes administering a chemotherapeutic agent or an anti-viral agent.

The compounds of the invention can be administered in combination with one or more additional therapeutic agents. The phrases "combination therapy", "combined with" and the like refer to the use of more than one medication or treatment simultaneously to increase the response. The GMPS inhibitor of the present invention might for example be used in combination with other drugs or treatment in use to treat cancer, immune diseases and disorders or viral infection. In various aspect, the compound is administered prior to, simultaneously with or following the administration of the chemotherapeutic agent or anti-viral agent.

The term "anti-cancer therapy" refers to any therapy or treatment that can be used for the treatment of a cancer. Anti-cancer therapies include, but are not limited to, surgery, radiotherapy, chemotherapy, immune therapy and targeted therapies.

Examples of chemotherapeutic agents or anti-cancer agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fiuorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, natalizumab Gilotrif (afatinib), Lynparza (olaparib), Perj eta (pertuzumab), Otdivo (nivolumab), Bosulif (bosutinib), Cabometyx (cabozantinib), Ogivri (trastuzumab-dkst), Sutent (sunitinib malate), Adcetris (brentuximab vedotin), Alecensa (alectinib), Calquence (acalabrutinib), Yescarta (ciloleucel), Verzenio (abemaciclib), Keytruda (pembrolizumab), Aliqopa (copanlisib), Nerlynx (neratinib), Imfinzi (durvalumab), Darzalex (daratumumab), Tecentriq (atezolizumab), and Tarceva (erlotinib). Examples of immunotherapeutic agent include, but are not limited to, interleukins (I1-2, I1-7, I1-12), cytokines (Interferons, G-CSF, imiquimod), chemokines (CCL3, CC126, CXCL7), immunomodulatory imide drugs (thalidomide and its analogues).

A viral infection can be treated using antiviral drugs that are specific for to the viral agent. The terms "anti-viral drug", "anti-viral agent", and the like are used without any distinction and refer to the drugs used to inhibit virus development and replication. Antiviral agents also include antiviral drugs based on monoclonal antibodies, and viricides, which deactivate or destroy virus particles, either inside or outside the body.

Anti-viral agents include but are not limited to, Abacavir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Norvir, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, and Zidovudine.

In another embodiment, the invention provides a method of suppressing an immune response in a subject comprising administering a compound of Formula (I) or Formula (II), as provided in Table 1 or an optically pure stereoisomer or pharmaceutically acceptable salt thereof. In certain aspects, the compound is at least one of compounds 1-5 as shown in Table 2 or an optically pure stereoisomer or pharmaceutically acceptable salt thereof.

The immune system is a system of biological structures and processes within an organism that protects against disease. This system is a diffuse, complex network of interacting cells, cell products, and cell-forming tissues that protects the body from pathogens and other foreign substances, destroys infected and malignant cells, and removes cellular debris: the system includes the thymus, spleen, lymph nodes and lymph tissue, stem cells, white blood cells, antibodies, and lymphokines. B cells or B lymphocytes are a type of lymphocyte in the humoral immunity of the adaptive immune system and are important for immune surveillance. T cells or T lymphocytes are a type of lymphocyte that plays a central role in cell-mediated immunity. In contrast, the B cell antigen-specific receptor is an antibody molecule on the B cell surface, and recognizes whole pathogens without any need for antigen processing. Each lineage of B cell expresses a different antibody, so the complete set of B cell antigen receptors represent all the antibodies that the body can manufacture.

The term "immune response" refers to an integrated bodily response to an antigen and preferably refers to a cellular immune response or a cellular as well as a humoral immune response. The immune response may be protective/preventive/prophylactic and/or therapeutic.

In various aspects, the subject has an autoimmune disorder, an inflammatory disorder, askylosing spondylitis or an organ and tissue transplant. In many aspects, the compound inhibits guanosine monophosphate synthetase.

"Immune disorder" or "immune disease" refer to any medical conditions characterized by a dysfunction of the immune system. Autoimmune diseases are characterized by the abnormal activation and proliferation of self-reactive T- and B-cells, capable of being reactive against substances and tissues normally present in the body (autoimmunity). Self-antigen reactivity can induce damage to or destruction of tissues, alteration of organ growth, and/or alteration of organ function.

Auto-immune and inflammatory diseases and disorders include, but are not limited to, Acute disseminated encephalomyelitis (ADEM), Addison's disease, Agammaglobulinemia, Alopecia areata, Amyotrophic lateral sclerosis (aka Lou Gehrig's disease), Ankylosing Spondylitis, Antiphospholipid syndrome, Antisynthetase syndrome, Arthritis, Asthma; Atherosclerosis Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Diverticulitis, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, graft versus host disease, Gout, Graves' disease, Guillain-Barré syndrome, Hashimoto's encephalopathy, Hashimoto's thyroiditis, Henoch-Schonlein purpura, Hepatitis, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Irritable bowel syndrome, Juvenile idiopathic arthritis aka Juvenile rheumatoid arthritis, Kawasaki's disease, Lambert-Eaton myasthenic syndrome, Laryngitis, Leukocytoclastic vasculitis, Lichen planus, Lichen sclerosus, Linear IgA disease, Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Myopathies, Meniere's disease, Narcolepsy, Nephritis, Neuromyelitis optica, Neuromyotonia, Ocular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pelvic inflammatory disease, Pemphigus vulgaris, Perivenous encephalomyelitis, Pernicious anaemia, Pharyngitis, Pleurisy, POEMS syndrome, Polyarteritis nodosa, Polymyalgia rheumatica, Polymyositis, Primary biliary cirrhosis, Primary sclerosing cholangitis, Progressive inflammatory neuropathy, Prostatitis, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome, Schnitzler syndrome, Scleritis, Scleroderma, Seborrheic dermatitis, Serum Sickness, Sinusitis, Sjögren's syndrome, Splenitis, Spondyloarthropathy, Stiff person syndrome, Still's disease, Subacute bacterial endocarditis (SBE), Susac's syndrome, Sweet's syndrome, Sydenham chorea, Sympathetic ophthalmia, Systemic lupus erythematosus, Takayasu's arteritis, Temporal arteritis, Thrombocytopenia, thyroiditis, Tolosa-Hunt syndrome, Transverse myelitis, Ulcerative colitis, Undifferentiated spondyloarthropathy, Urticarial vasculitis, Vasculitis, Vitiligo, Wegener's granulomatosis, Familial Mediterranean fever (FMF), Hyperimmunoglobulinemia D with recurrent fever (HIDS), TNF receptor associated periodic syndrome (TRAPS), Muckle-Wells syndrome (CAPS, urticaria deafness amyloidosis), Familial cold urticarial, Neonatal onset multisystem inflammatory disease, Periodic fever, aphthous stomatitis, pharyngitis and adenitis (PFAPA syndrome), Blau syndrome, Pyogenic sterile arthritis, pyoderma gangrenosum, acne (PAPA), Deficiency of the interleukin-1-receptor antagonist (DIRA), Allergic reactions, Crohn's disease and Gout.

Immunosuppressive drugs or immunosuppressive agents or antirejection medications are drugs that inhibit or prevent activity of the immune system. Immunosuppressive agents are used in indications were suppression of the immune system is desired. Such indications include autoimmune disorders (psoriasis, lupus, rheumatoid arthritis, Crohn's disease, multiple sclerosis, alopecia areata, myasthenia gravis, vitiligo, granulomatosis, sarcoidosis, focal segmental glomerulosclerosis, Behcet's disease, pemphigus, ulcerative colitis), non-autoimmune inflammatory diseases (asthma, allergies), askylosing spondylitis and in organ and tissue transplantation. Immunosuppressive agents include corticosteroids, calineurin inhibitors, mTOR inhibitors, IMDH inhibitors, biologic agents and monoclonal antibodies.

Examples of specific immunosuppressive agents include, but are not limited to, prednisone (Deltasone, Orasone), budesonide (Entocort EC), prednisolone (Millipred), cyclosporine (Neoral, Sandimmune, SangCya), tacrolimus (Astagraf XL, Envarsus XR, Prograf), sirolimus (Rapamune), everolimus (Afinitor, Zortress), azathioprine (Azasan, Imuran), leflunomide (Arava), mycophenolate (CellCept, Myfortic), abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), daclizumab (Zinbryta), and muromonab (Orthoclone OKT3).

In yet another embodiment, the invention provides a pharmaceutical composition comprising a compound of Formula (I) or Formula (II), as provided in Table 1, or an optically pure stereoisomer or pharmaceutically acceptable salt and a pharmaceutically acceptable carrier. In certain aspects, the compound is at least one of compounds 1-5 as shown in Table 2 or an optically pure stereoisomer or pharmaceutically acceptable salt thereof.

By "pharmaceutically acceptable" it is meant the carrier, diluent or excipient must be compatible with the other ingredients of the formulation and not deleterious to the recipient thereof. For example, the carrier, diluent, or excipient or composition thereof may be administered to a subject along with a GMPS inhibitor of the invention without causing any undesirable biological effects or interacting in an undesirable manner with the GMPS inhibitor of the pharmaceutical composition in which it is contained.

Presented below are examples discussing novel guanosine monophosphate synthetase inhibitors, their potency and efficacy against cancer cells, contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used

EXAMPLES

Example 1

Development of Novel Guanosine Monophosphate Synthetase Inhibitors

Guanosine monophosphate synthetase (GMPS) is a bi-domain enzyme whose glutaminase domain generates ammonia which is transferred to the synthetase domain to convert XMP into GMP, a nucleotide precursor to RNA. Accordingly, and as illustrated in FIG. 1, GMPS plays important roles in cell division and proliferation as well as in viral infection.

Given the lack of potent and specific GMPS inhibitors, a series of novel compounds were developed and the characterization of their ability to induce the inhibition of GMPS enzymatic activity was assessed.

As illustrated in FIG. 2, the compounds that were developed have a structure as described in the two scaffolds (I) and (II). In the general structures (I) and (II), X is N or CH, $R_1$ is (alkyl, acyl, alkoxy, halo, amino, amido, alkenyl, and alkynyl), and $R_2$ is (alkyl, acyl, alkoxy, halo, amino, amido, alkenyl, and alkynyl).

As illustrated in FIG. 3, five compounds having the compound structure (1-5) based on the two scaffolds (I) and (II), 4-anilinoquinazoline or N-phenylbenzamide, were synthesized using previously reported conditions with modifications.

Example 2

Evaluation of the GMPS Inhibitors Potency

The potency of the five compounds was tested against recombinant GMPS in an enzymatic assay by monitoring UV absorbance at 290 nm and by determining an IC50. The IC50 values obtained are summarized in Table 3. Three compounds (1, 2 and 4) inhibited GMPS with nanomolar IC50 values while the other two (3 and 5) were found less active. The structure-activity relationship (SAR) indicated that the chloroacetamide group is essential for potent binding to GMPS.

TABLE 3

$IC_{50}$ values of the compounds against recombinant human GMPS in an enzymatic assay.

| Compound | $IC_{50}$ (nM) |
| --- | --- |
| 1 | 6.2 |
| 2 | 23 |
| 3 | >1000 |
| 4 | 98 |
| 5 | >1000 |

Example 3

Evaluation of Compound 1 Covelent Binding to GMPS in Live Cells

In order to evaluate the binding ability of the compound to GMPS in live cells, the most potent inhibitor in the series, Compound 1, was evaluated for its covalent binding to GMPS in live cells.

HEK293 cells were treated with various concentrations of compound 1 for 20 minutes. Cells were washed with DPBS (Dubelco Phosphate Saline Buffer), harvested via centrifugation, and then lysed using NP40-based buffer. The resulting cell lysate was subjected to Cu catalyzed azide-alkyne cycloaddition reaction (CuAAC) with TAMRA azide before being resolved by SDS PAGE and visualized for TAMRA fluorescence. As illustrated in FIG. 4A, a prominent band was observed at approximately 75 kDa, matching the size of GMPS. This result indicated that compound 1 bound covalently to GMPS, as expected from the observed importance of its harbored electrophile for binding to the target. Furthermore, the dose response indicated that compound 1 covalently bound GMPS at low nanomolar concentrations and that the binding saturated at approximately 100 nM.

In order to confirm the binding of compound 1 to GMPS, a pull-down experiment with compound 1 was performed. The band at 75 kDa was enriched and analyzed through liquid chromatography/mass spectrometry (LC/MS/MS), which confirmed that the band at 75 kDa was indeed GMPS (FIG. 4B). These data suggested that compound 1 potently and specifically bound to GMPS in live cells.

Example 4

Evaluation of Compound 1 Efficacy to Inhibit Cancer Cells Survival

In order to assess the efficacy of compound 1 to inhibit cancer cells survival, Compound 1 was screened against eight distinct cancer cell lines and the effects on cell proliferation were measured using a viability assay based on a fluorescent dye Sulforhodamin B. As illustrated in FIG. 5, and as quantifies in Table 4, it was found that Compound 1 caused >50% cell death across all the eight cell lines tested. These results suggested that GMPS inhibitors like compound 1 exhibit broad-spectrum anti-cancer activity.

TABLE 4

Effects of compound 1 on the survival of eight different cancer types.

| Cancer cell type | Cell line | Cell survival |
| --- | --- | --- |
| Leukemia | HL-60(TB) | −58.4 |
| Non-Small Cell Lung Cancer | NCI-H23 | −66.8 |
| Colon Cancer | HT29 | −78.6 |
| CNS Cancer | SF-539 | −86.6 |
| Melanoma | SK-MEL-5 | −92.8 |
| Ovarian Cancer | OVCAR-5 | −70.1 |
| Renal Cancer | UO-31 | −87.8 |
| Breast Cancer | BT-549 | −68.9 |

(Negative values represent cell mortality percentage)

Although the invention has been described with reference to the above examples, it will be understood that modifications and variations are encompassed within the spirit and scope of the invention. Accordingly, the invention is limited only by the following claims.

What is claimed is:
1. A compound selected from the group consisting of:
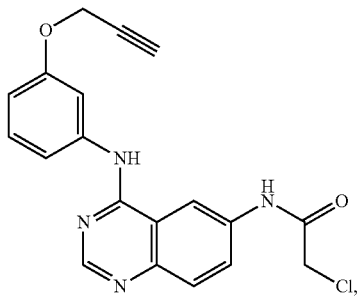
1
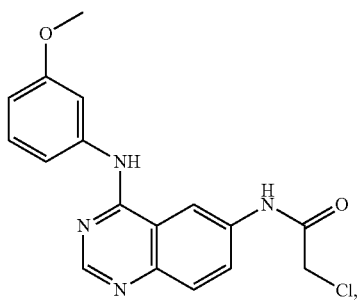
2
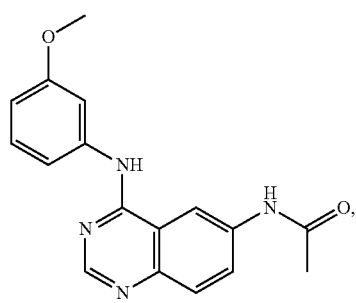
3
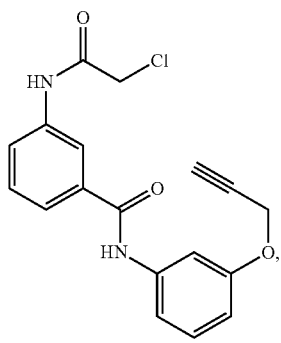
4
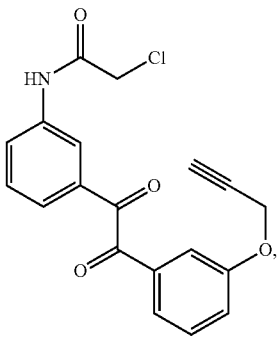
5
or an optically pure stereoisomer or pharmaceutically acceptable salt thereof.
2. The compound of claim 1, wherein the compound is:
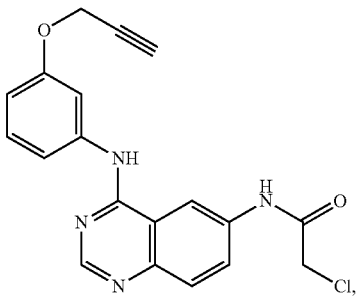
1
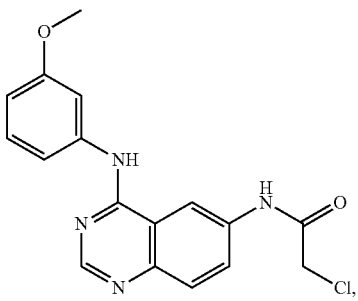
2
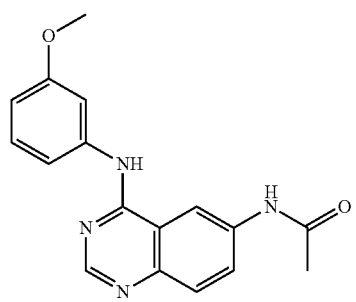 [SMILES: COc1cccc(Nc2ncnc3ccc(NC(C)=O)cc23)c1]
3
or a pharmaceutically acceptable salt thereof.

3. The compound of claim 1, wherein the compound is:

[Structure 4: N-(3-(3-chloroacetamido)benzamido)phenyl prop-2-yn-1-yl ether]

[Structure 5: 1-(3-chloroacetamidophenyl)-2-(3-(prop-2-yn-1-yloxy)phenyl)ethane-1,2-dione]

or a pharmaceutically acceptable salt thereof.

4. A pharmaceutical composition comprising the compound of claim 1 and a pharmaceutically acceptable carrier.

5. The pharmaceutical composition of claim 4, wherein the compound is selected from the group consisting of:

[Structure 1: 2-chloro-N-(4-((3-(prop-2-yn-1-yloxy)phenyl)amino)quinazolin-6-yl)acetamide]

[Structure 2: 2-chloro-N-(4-((3-methoxyphenyl)amino)quinazolin-6-yl)acetamide]

[Structure 3: N-(4-((3-methoxyphenyl)amino)quinazolin-6-yl)acetamide]

or a pharmaceutically acceptable salt thereof.

6. The pharmaceutical composition of claim 4, wherein the compound is:

[Structure 4]

[Structure 5]

or a pharmaceutically acceptable salt thereof.

* * * * *